(12) United States Patent
Gotoh et al.

(10) Patent No.: US 7,846,227 B2
(45) Date of Patent: Dec. 7, 2010

(54) VEHICLE-MOUNTED AIR PURIFIER

(75) Inventors: Hidetoshi Gotoh, Yamatokoriyami (JP); Yoshiko Gotoh, legal representative, Yamatokoriyama (JP); Yasunori Gotoh, legal representative, Yamatokoriyama (JP); Toshiyuki Gotoh, legal representative, Nara (JP); Akira Yamamoto, Yao (JP)

(73) Assignee: Sharp Kabushiki Kaisha, Osaka-shi (JP)

( * ) Notice: Subject to any disclaimer, the term of this patent is extended or adjusted under 35 U.S.C. 154(b) by 1063 days.

(21) Appl. No.: 10/570,304

(22) PCT Filed: Sep. 16, 2004

(86) PCT No.: PCT/JP2004/013543

§ 371 (c)(1),
(2), (4) Date: Nov. 9, 2006

(87) PCT Pub. No.: WO2005/028227

PCT Pub. Date: Mar. 31, 2005

(65) Prior Publication Data

US 2007/0167124 A1    Jul. 19, 2007

(30) Foreign Application Priority Data

Sep. 22, 2003   (JP) ............................... 2003-329690

(51) Int. Cl.
*B60H 3/00*   (2006.01)
*C01B 13/11*  (2006.01)

(52) U.S. Cl. .................... 55/385.3; 95/78; 361/230; 361/231; 361/233; 96/62; 96/63; 96/64

(58) Field of Classification Search ............... 55/385.3, 55/418, 434, 465, DIG. 28; 95/31, 267, 78; 454/108, 147; 180/68.3, 69.25; 361/230, 361/231, 233; 96/62–64
See application file for complete search history.

(56) References Cited

U.S. PATENT DOCUMENTS 1,345,790 A * 7/1920 Lodge ......................... 96/62

(Continued)

FOREIGN PATENT DOCUMENTS

DE           10111447 A1    9/2002

(Continued)

*Primary Examiner*—Duane Smith
*Assistant Examiner*—Minh-Chau Pham
(74) *Attorney, Agent, or Firm*—Birch, Stewart, Kolasch & Birch, LLP

(57) ABSTRACT

A vehicle-mounted air purifier 1 includes a main unit incorporating an ion generator. The main unit is removably arranged within a passenger space inside a vehicle. For example, if a beverage container holder 90 is provided inside the vehicle, the main unit can be removably arranged within the passenger space when given a cylindrical shape that permits it to be held in the beverage container 90. The power from which the vehicle-mounted air purifier 1 operates can be taken from a cigarette lighter power outlet 91 provided inside the vehicle through a connection cable 92. The main unit is thus arranged directly within the passenger space, and the ions generated by the ion generator inside are fed into the passenger space with higher efficiency. The main unit is removably arranged as an independent unit. Thus, even when the ion generator breaks down or otherwise its replacement becomes necessary, the arranged ion generator can be removed readily and replaced easily.

17 Claims, 12 Drawing Sheets

U.S. PATENT DOCUMENTS

| | | | | |
|---|---|---|---|---|
| 3,611,414 A | * | 10/1971 | Frank | 347/123 |
| 4,253,852 A | * | 3/1981 | Adams | 96/58 |
| 5,012,159 A | * | 4/1991 | Torok et al. | 315/111.91 |
| 5,180,404 A | * | 1/1993 | Loreth et al. | 96/56 |
| 5,618,323 A | * | 4/1997 | Shearn et al. | 55/385.3 |
| 5,762,665 A | * | 6/1998 | Abrahamian et al. | 55/385.3 |
| 6,785,114 B2 | * | 8/2004 | Gorczyca et al. | 361/231 |
| 6,953,556 B2 | * | 10/2005 | Taylor et al. | 422/186.04 |
| 6,964,698 B1 | * | 11/2005 | Davis et al. | 96/52 |
| 7,273,515 B2 | * | 9/2007 | Yuen | 96/16 |
| 7,295,418 B2 | * | 11/2007 | Vernitsky et al. | 361/230 |
| 7,368,003 B2 | * | 5/2008 | Crapser et al. | 96/52 |
| 7,408,562 B2 | * | 8/2008 | Kotsuji | 347/123 |
| 7,461,835 B2 | * | 12/2008 | Petz et al. | 261/119.1 |
| 2002/0139251 A1 | * | 10/2002 | Simmons | 96/134 |
| 2003/0029319 A1 | * | 2/2003 | Ninomiya et al. | 96/63 |
| 2005/0087071 A1 | * | 4/2005 | Petz et al. | 96/52 |

FOREIGN PATENT DOCUMENTS

| | | |
|---|---|---|
| EP | 0 321 419 A2 | 6/1989 |
| JP | 6-289976 A | 10/1994 |
| JP | 10-152307 A | 6/1998 |
| JP | 10-180139 A | 7/1998 |
| JP | 2000-43632 A | 2/2000 |
| JP | 2002-252072 A | 9/2002 |
| JP | 2003-151718 A | 5/2003 |
| JP | 2003-153995 A | 5/2003 |

* cited by examiner

FIG.4A
FIG.4B
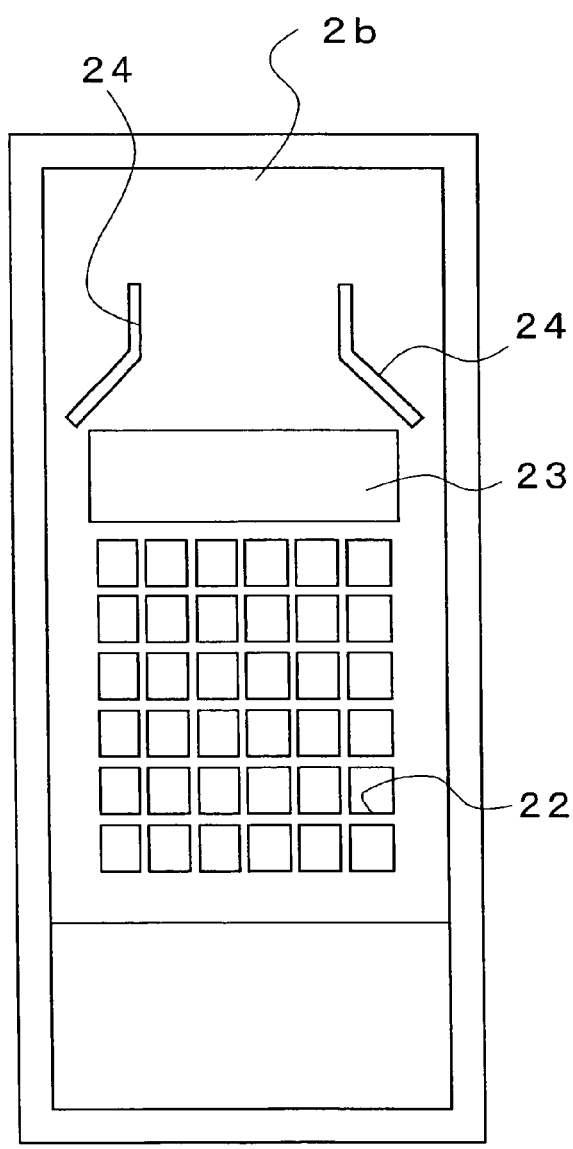
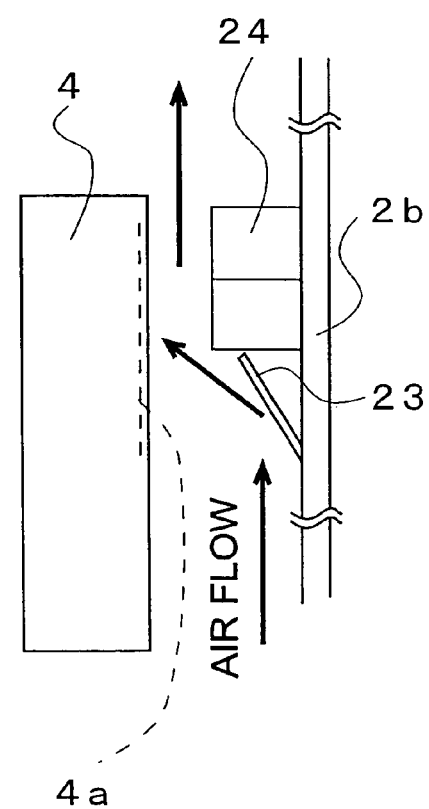

3a  3b  3c

VEHICLE-MOUNTED AIR PURIFIER

TECHNICAL FIELD

The present invention relates to a vehicle-mounted air purifier that purifies the air inside a vehicle by feeding air containing both positive and negative ions into the inside of the vehicle.

BACKGROUND ART

There have conventionally been proposed various ion generators that generate both positive and negative ions. For example, Patent Publication 1 listed below discloses an example in which such an ion generator is applied to a vehicle. Specifically, as shown in FIG. 12, inside the interior walls 101 and 102 that form the passenger space inside a vehicle, there is formed a passage 103 through which to feed air-conditioned air into the passenger. Inside this passage 103, an ion generator 104 is arranged, so that air containing the ions generated by the ion generator 104 is fed through wind direction control plates 105 into the passenger space inside the vehicle.
Patent Publication 1: J-P-A-2003-151718

DISCLOSURE OF THE INVENTION

Problems to be Solved by the Invention

According to Patent Publication 1, the ion generator 104 is arranged in a space (the passage 103) that is secured separately from the passenger space, into which ions are intended to be fed, and that is located opposite to the passenger space with respect to the wind direction control plates 105. Thus, the ions generated by the ion generator 104, before being discharged into the passenger space, repeatedly collide with the wall surface inside the passage 103 and with the wind direction control plates 105. This causes ions to be absorbed by the wall surface and the like, and thus eventually causes the number of ions that are discharged into the passenger space to reduce. Thus, disadvantageously, the construction according to Patent Publication 1 suffers from poor ion feed efficiency.

Moreover, according to Patent Publication 1, the ion generator 104 remains fixed inside the passage 103. Thus, for example, when the ion generator 104 breaks down and its replacement becomes necessary, disadvantageously, it takes much trouble to remove the ion generator 104 from the vehicle.

In view of the conventionally experienced inconveniences discussed above, it is an object of the present invention to provide a vehicle-mounted air purifier that permits the ions generated by an ion generator to be fed into the passenger space with high efficiency and that permits a breakdown or the like of the ion generator to be taken care of easily.

Means for Solving the Problem

To achieve the above object, according to the present invention, in a vehicle-mounted air purifier mounted on a vehicle and including a main unit incorporating an ion generator that generates positive ions, negative ions, or both positive and negative ions, the main unit is removably arranged within the passenger space inside the vehicle.

With this configuration, the main unit incorporating the ion generator is arranged directly within the passenger space inside the vehicle (for example, in a beverage container holder). This greatly reduces the number of times that the ions (positive and/or negative ions) generated by the ion generator collide with exterior components as compared with, for example, when the ion generator is arranged in a passage inside an outlet of air-conditioned air. Thus, assuming that the ion generating performance of the ion generator (the number of ions it generates per unit time) is constant, it is possible to feed ions into the passenger space with higher efficiency than can conventionally be achieved.

Moreover, the main unit is arranged within the passenger space so that it is removable as an independent unit. Thus, even when the ion generator breaks down or otherwise its replacement becomes necessary, the arranged ion generator can be removed readily and replaced easily. Moreover, the replacement can be performed easily even by a nonprofessional without expertise on repair of vehicles. Moreover, a vehicle that is originally not equipped with an ion generator can later be fitted with one. This helps enhance usability.

Advantages of the Invention

According to the present invention, it is possible to feed the ions generated by an ion generator into the inside of a vehicle with higher efficiency than can conventionally be achieved, and it is possible to replace the ion generator easily when it breaks down or in other circumstances.

BRIEF DESCRIPTION OF DRAWINGS

FIG. 4A A plan view of the inner surface of the rear housing member constituting part of the main unit.

FIG. 4B A vertical sectional view of part of the rear housing member.

Figure 1:
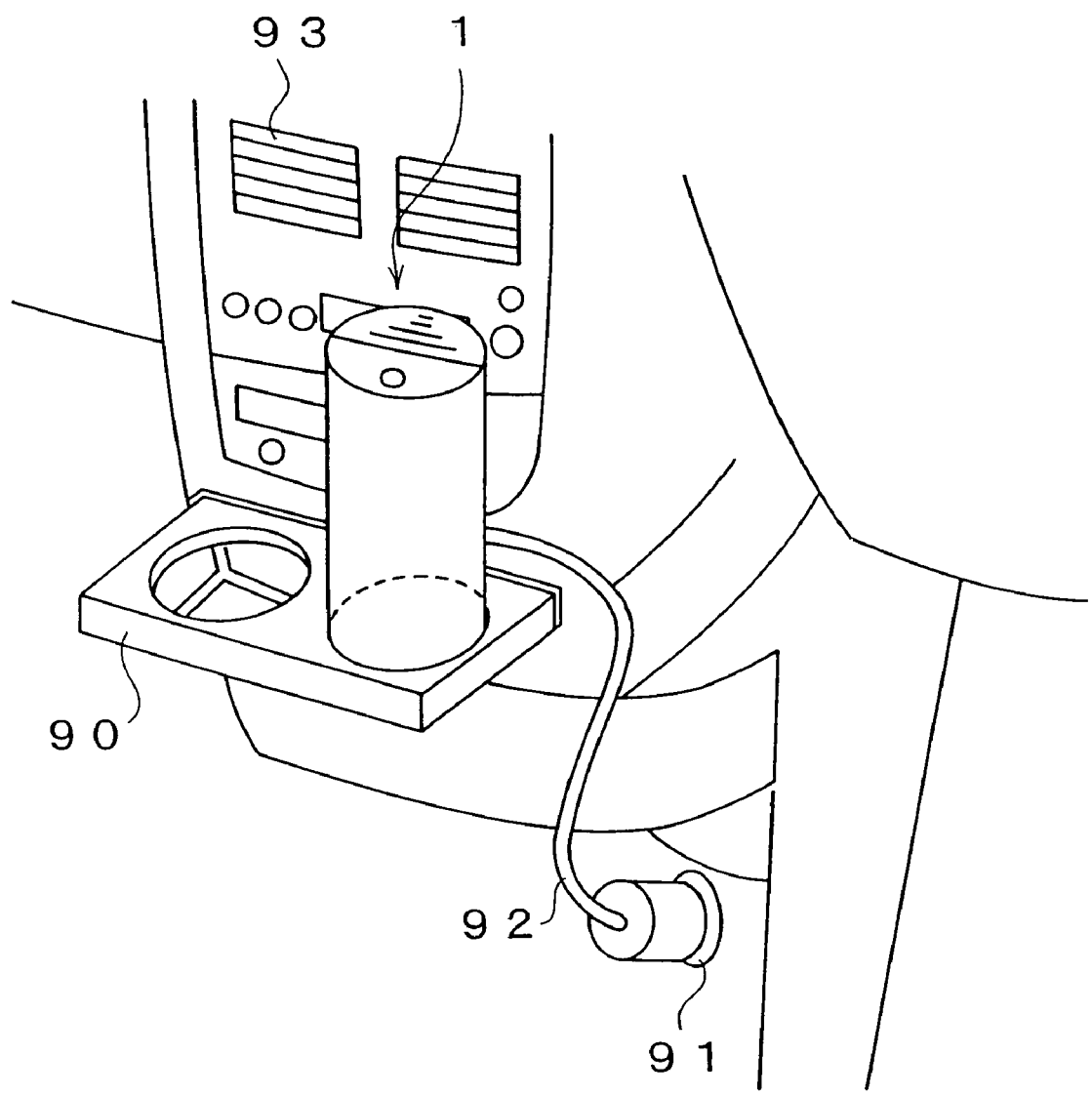
FIG. 1 A perspective view showing how a vehicle-mounted air purifier embodying the invention is held in a beverage container holder provided inside a vehicle.

LIST OF REFERENCE SYMBOLS 1 vehicle-mounted air purifier
2 main unit
2a front housing member (separate housing member)
2b rear housing member (separate housing member)
3 light guide member 4 ion generator
4a discharge surface
5 display circuit board
5a cut portions
9 blowing means
21 outlet (second outlet)
23 guide plate (guiding means)
24 compressing member
25 plug receptacle (connection portion)
27 cable clearances
35 step-up coil
36 shielding member
36a shielding member
36b shielding member
52 LED (light-emitting element)
53 LED (light-emitting element)
90 beverage container holder
91 cigarette lighter power outlet.
92 connection cable (wiring)
93 outlet (first outlet)

BEST MODE FOR CARRYING OUT THE INVENTION

An embodiment of the present invention will be described with reference to the drawings.

(1-1. Vehicle-Mounted Air Purifier)

FIG. 1 shows a vehicle-mounted air purifier 1 embodying the invention, in a state held in a beverage container holder 90 provided inside a vehicle. The vehicle-mounted air purifier 1 incorporates an ion generator, which will be described later (see FIG. 2). The vehicle-mounted air purifier 1 is removably arranged within the passenger space inside a vehicle, and is, as shown in the figure, given a shape (for example, cylindrical) that permits it to be held in the beverage container holder 90. The beverage container holder 90 may be one with which the vehicle is originally equipped when shipped out or one that is bought separately and fitted to the vehicle later.

The vehicle-mounted air purifier 1 may be arranged wherever else within the passenger space inside the vehicle than in the above-mentioned beverage container holder permits storage or placement of beverage containers, small articles, and the like, for example in a small luggage space between the driver's and assistant's seats or in a beverage box for rear seats. Now, the construction of the vehicle-mounted air purifier 1 will be described in detail.

Figure 2:
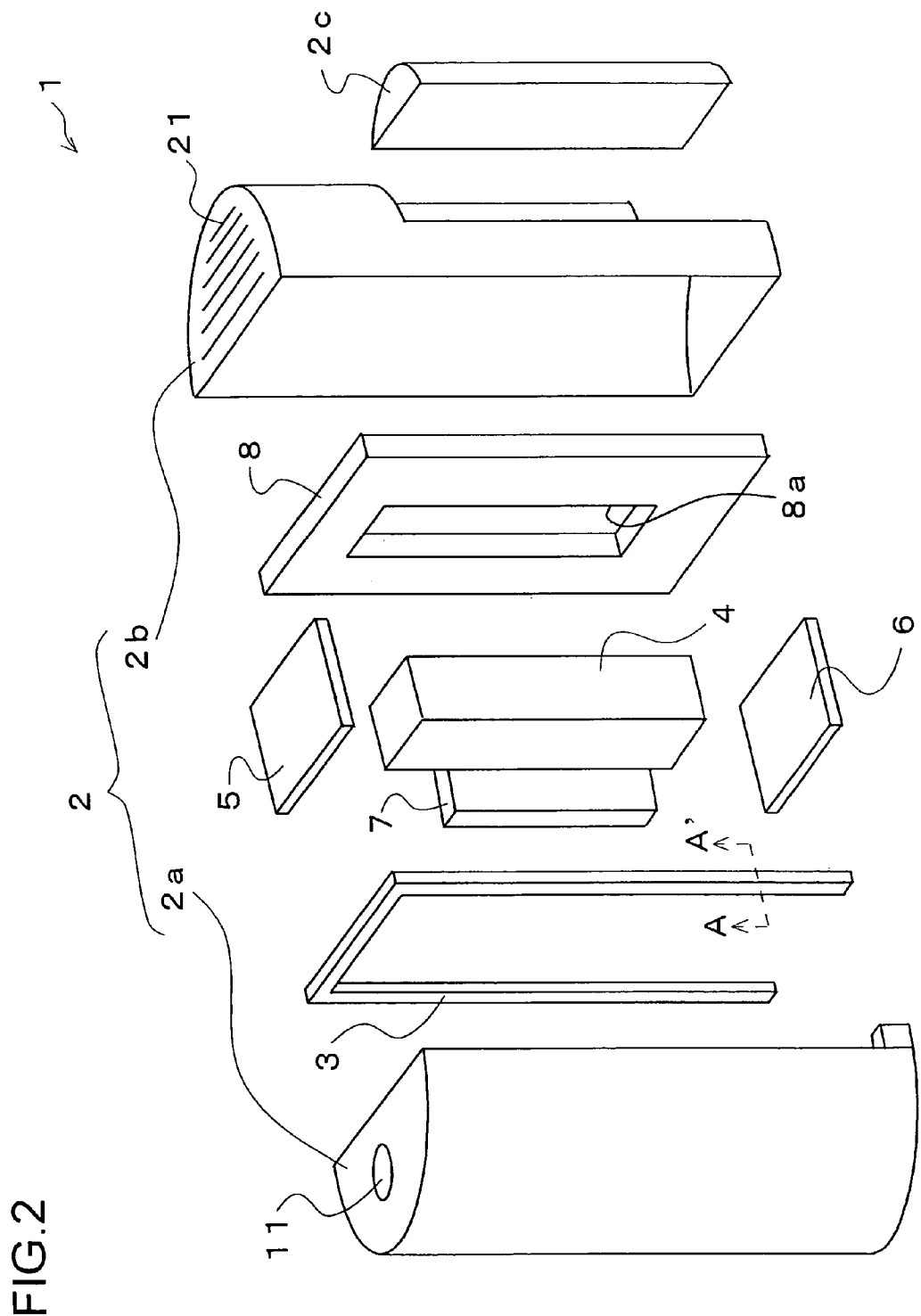
FIG. 2 An exploded perspective view showing an outline of the construction of the vehicle-mounted air purifier.

FIG. 2 is an exploded perspective view showing an outline of the construction of the vehicle-mounted air purifier 1. The vehicle-mounted air purifier 1 includes a main unit 2, a light guide member 3, an ion generator 4, a display circuit board 5, a power supply circuit board 6, a control circuit board 7, a support plate 8, and blowing means 9 (see FIG. 11).

(1-2. Main Unit)

The main unit 2 is given a shape (for example, cylindrical) that permits it to fit into the beverage container holder 90. A beverage container holder 90 is often provided for a commercially available vehicle, already when it is shipped out, by its own manufacturer; even when this is not the case, one built as a separate unit is often bought separately and fitted to the vehicle later. Accordingly, giving the main unit 2 a shape that permits it to fit into the beverage container holder 90 permits the main unit 2 to be held in the beverage container holder 90 so that the air inside the vehicle can easily be purified by the vehicle-mounted air purifier 1. This benefit can surely be obtained particularly when the main unit 2 is given a cylindrical shape that permits it to fit into beverage container holder 90. Moreover, by designing the main unit 2 so that it can be held in the beverage container holder 90, it is possible to achieve purification of the air inside the vehicle by effectively using the beverage container holder 90 provided inside the vehicle. The main unit 2 may be given any other shape, for example, rectangular, so long as the shape permits it to be held in the beverage container holder 90.

The main unit 2 is composed of a plurality of separate housing members that are divided along a plane perpendicular to the top and bottom faces thereof. Specifically, here, the main unit 2 is composed of a front housing member 2a and a rear housing member 2b bonded together. On the back face of the rear housing member 2b, a lid member 2c is provided so as to be separable therefrom.

(1-2-1 Front Housing Member)

On the top face of the front housing member 2a, an operation button 11 is formed. When the user operates this operation button 11 by pressing it, the operation of the vehicle-mounted air purifier 1 is switched among different modes. To the top face of the front housing member 2a is bonded a display sheet (not illustrated) bearing indications corresponding to the modes that can be switched with the button.

In this embodiment, the operation of the vehicle-mounted air purifier 1 can be switched among the following modes: "automatic mode", "clean mode", "ion control mode", and "out of operation." In "automatic" mode, operation is performed alternately in "clean mode" and "ion control mode" at regular time intervals (for example, at 15-minute intervals). In "clean mode", operation is so performed as to generate roughly equal numbers of positive and negative ions. In "ion control mode", with a view to obtaining a proper ion balance inside the vehicle, operation is so performed as to generate negative ions in a higher proportion than positive ions, or to generate negative ions alone. Every time the operation button 11 is pressed, these different operation modes are switched from one to the next.

Figure 3:
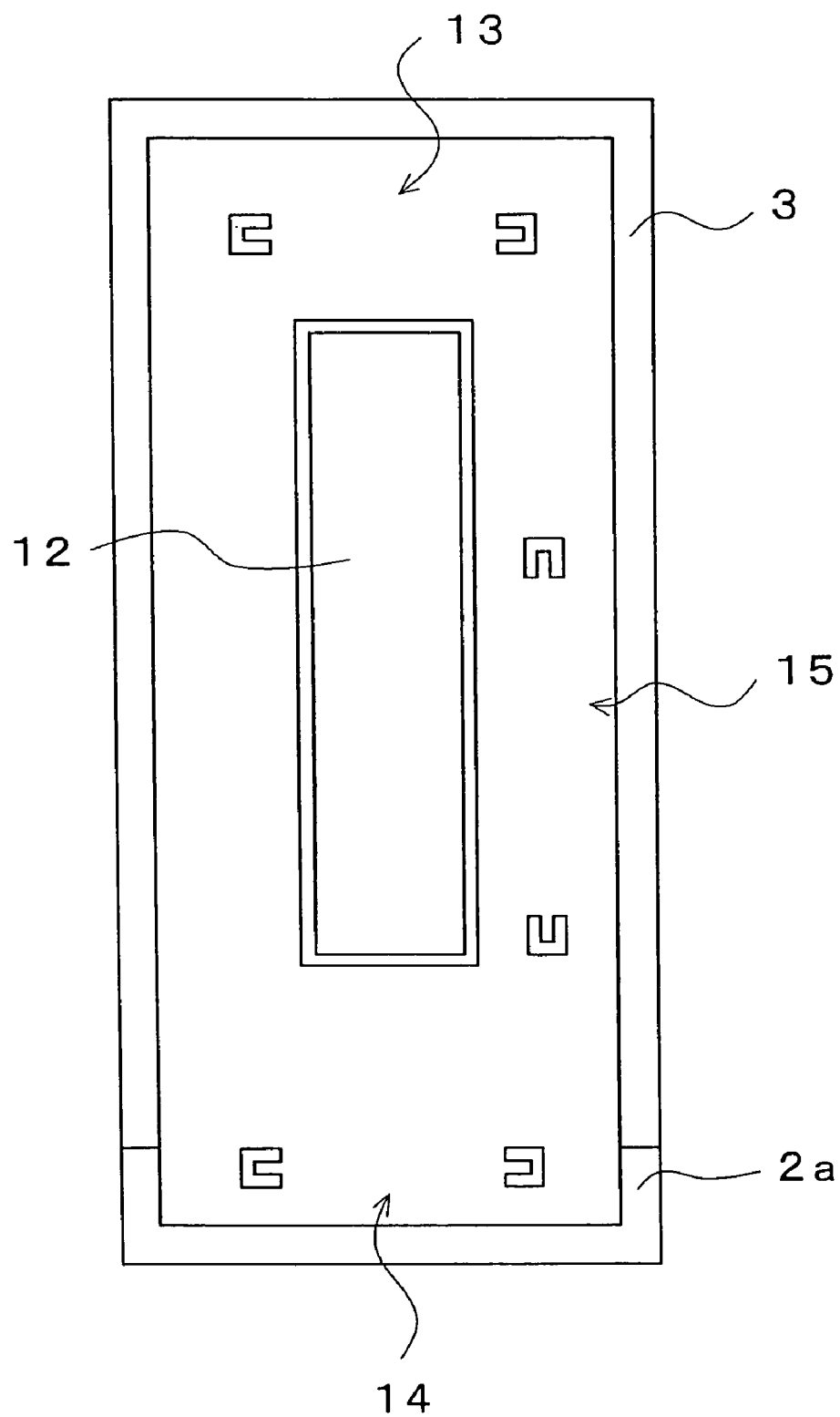
FIG. 3 A plan view of the inner surface of the front housing member constituting part of the main unit of the vehicle-mounted air purifier.

FIG. 3 is a plan view showing the inner surface of the front housing member 2a, with the light guide member 3 bonded on that face of the front housing member 2a at which it is bonded to the rear housing member 2b. At the center of the inner surface of the front housing member 2a, a ion generator support portion 12 for supporting the ion generator 4 is formed. The ion generator support portion 12 is so formed as to have a rectangular section and be vertically elongate along the shape of the ion generator 4. The ion generator 4 fits into the ion generator support portion 12, and is thereby supported.

Also formed on the inner surface of the front housing member 2a are a display circuit board support portion 13, a power supply circuit board support portion 14, and a control circuit board support portion 15. The display circuit board support portion 13 is for supporting the display circuit board 5, and is located above the ion generator support portion 12. The power supply circuit board support portion 14 is for supporting the power supply circuit board 6, and is located below the ion generator support portion 12. The control circuit board support portion 15 is for supporting the control circuit board 7, and is located by the side of the ion generator support portion 12. Each of these support portions is composed of a pair of ribs each having a grove into which the circuit board it supports is inserted.

In reality, in predetermined positions on the inner surface of the front housing member 2a, bosses for fixing the front and rear housing members 2a and 2b together are formed, though these are omitted in FIG. 3.

(1-2-2. Rear Housing Member)

As shown in FIG. 2, in the top face of the rear housing member 2b, an outlet 21 (a second outlet) is provided through which air containing the ions generated by the ion generator 4 incorporated in the main unit 2 are blown out. To make the outlet 21 blow the air frontward (toward the front housing member 2a), in the outlet 21 are arranged a plurality of slanted wings. In this embodiment, these wings are fixed; needless to say, these may be movable so as to permit adjustment of the air discharge direction in the front-rear and left-right directions.

Here, as shown in FIG. 1, in a case where the beverage container holder 90 provided inside the vehicle is located blow an outlet 93 (a first outlet) through which air for air-conditioning of the inside of the vehicle is blown out, the outlet 21 of the main unit 2 is so located that, when the main unit 2 is held in the beverage container holder 90, the above-mentioned air containing ions is mixed with the air for air-conditioning that is blown out through the outlet 93. That is, to permit the air blown out of the main unit 2 to be mixed with the air blown out through the outlet 93, the height-direction dimension of the main unit 2 is limited within a certain limit, and the outlet 21 is provided in the top face of the main unit 2 so designed.

With the location of the outlet 21 determined in this way, when the main unit 2 is held in the beverage container holder 90, even if the main unit 2 has rather poor air exhaustion performance, i.e., even if the blowing means 9 has only poor blowing performance, air containing the ions discharged out of the main unit 2 can be carried by the air for air-conditioning that is blown out through the outlet 93 so as to spread all around the inside of the vehicle. This helps make the blowing means 9 compact, and thus helps make the main unit 2 compact.

Figure 5:
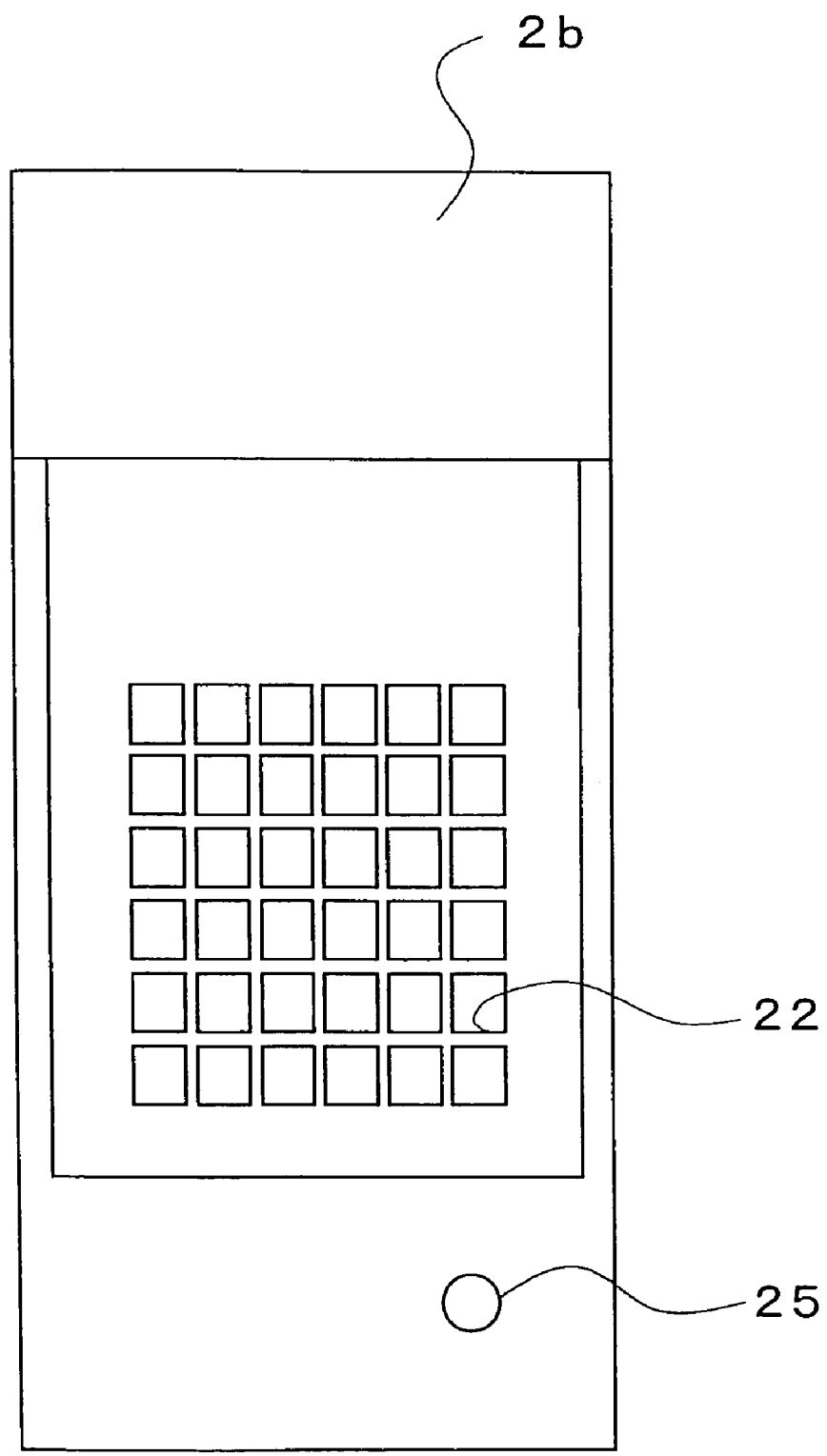
FIG. 5 A plan view of the rear housing member, as seen from the back side thereof.

Next, the interior of the rear housing member 2b will be described. FIG. 4A is a plan view of the rear housing member 2b as seen from in front (from the front housing member 2a side), and FIG. 4B is a vertical sectional view of part of the rear housing member 2b. FIG. 5 is a plan view of the rear housing member 2b, as seen from behind (from the back side thereof). The rear housing member 2b has an air introduction port 22, a guide plate 23 (guiding means), a compressing member 24, and a plug receptacle 25.

As the blowing means 9 is driven (see FIG. 11), the air sucked in through an inlet 26 formed in the lid member 2c is introduced through the air introduction port 22 into the main unit 2. The air introduction port 22 consists of a plurality of holes (for example, rectangular holes) that are arranged in a two-dimensional array.

The guide plate 23 guides the air blown out from the blowing means 9 in such a way that the air strikes the discharge surface of the ion generator 4 at an acute angle. That is, as shown in FIG. 4B, inside the main unit 2, the ion generator 4 is so arranged, by the ion generator support portion 12 (see FIG. 3), that the discharge surface 4a lies along the direction in which the blowing means 9 sends air (the direction from down to up), and the guide plate 23 is so slanted that the tip thereof points toward the discharge surface 4a relative to the inner surface of the rear housing member 2b. This permits the air fed from below by the blowing means 9 strikes the guide plate 23, by which the flow direction of the air is turned toward the discharge surface 4a, the air then flowing upward along the discharge surface 4a.

As will be described later, the ion generator 4 generates positive ions, negative ions, or both positive and negative ions by causing electric discharge on the discharge surface 4a. When electric discharge occurs on the discharge surface 4a, it is inevitably accompanied by discharge noise. It has been experimentally known that such discharge noise reduces as the angle at which air strikes the discharge surface 4a becomes closer to perpendicular thereto. However, if this angle is just perpendicular to the discharge surface 4a, the air that strikes it flows also in the direction (downward) opposite to the outlet 21. This reduces the efficiency with which the air (air containing the ions generated by the ion generator 4) is discharged out of the main unit 2.

Accordingly, providing the guide plate 23 as in this embodiment helps reduce the discharge noise on the discharge surface 4a and simultaneously avoid lowering the air discharge efficiency.

The compressing member 24 (a narrowing member) is for narrowing and thereby compressing the air that is discharged through the ion generator 4 out of the main unit 2. In this embodiment, the compressing member 24 forms an air passage such that the area through which the air fed from the blowing means 9 to the ion generator 4 passes is smaller than the area through which the air discharged through the ion generator 4 out of the main unit 2. To form such an air passage, the compressing member 24 is composed of two flat plates that are bent.

The provision of this compressing member 24 permits the air that is discharged through the ion generator 4 out of the main unit 2 to be compressed (narrowed) by the compressing member 24, and thus gives the air increased flow speed when it is discharged outward. Thus, even when the blowing means 9 is small and has poor blowing performance, sufficient air containing the ion generated inside the main unit 2 can be discharged out of it. Thus, it is possible to make the vehicle-mounted air purifier 1 satisfactorily compact while maintaining the performance thereof in producing positive and negative ions.

The plug receptacle 25 shown in FIG. 5 serves as a connection portion that is connected by way of a connection cable 92 (wiring) to a cigarette lighter power outlet 91 (see FIG. 1 provided inside the vehicle. The plug receptacle 25 is provided on the back side of the rear housing member 2b (the lid member 2c side thereof). The provision of this plug receptacle 25 permits the vehicle-mounted air purifier 1 to be driven with electric power fed from the cigarette lighter power outlet 91.

The vehicle-mounted air purifier 1 may be operated from a battery, or may be switched between operation from a battery and operation from electric power fed from the cigarette lighter power outlet 91. The vehicle-mounted air purifier 1 may be rechargeable from the cigarette lighter power outlet 91.

(1-2-3. Lid Member)

Figure 6:
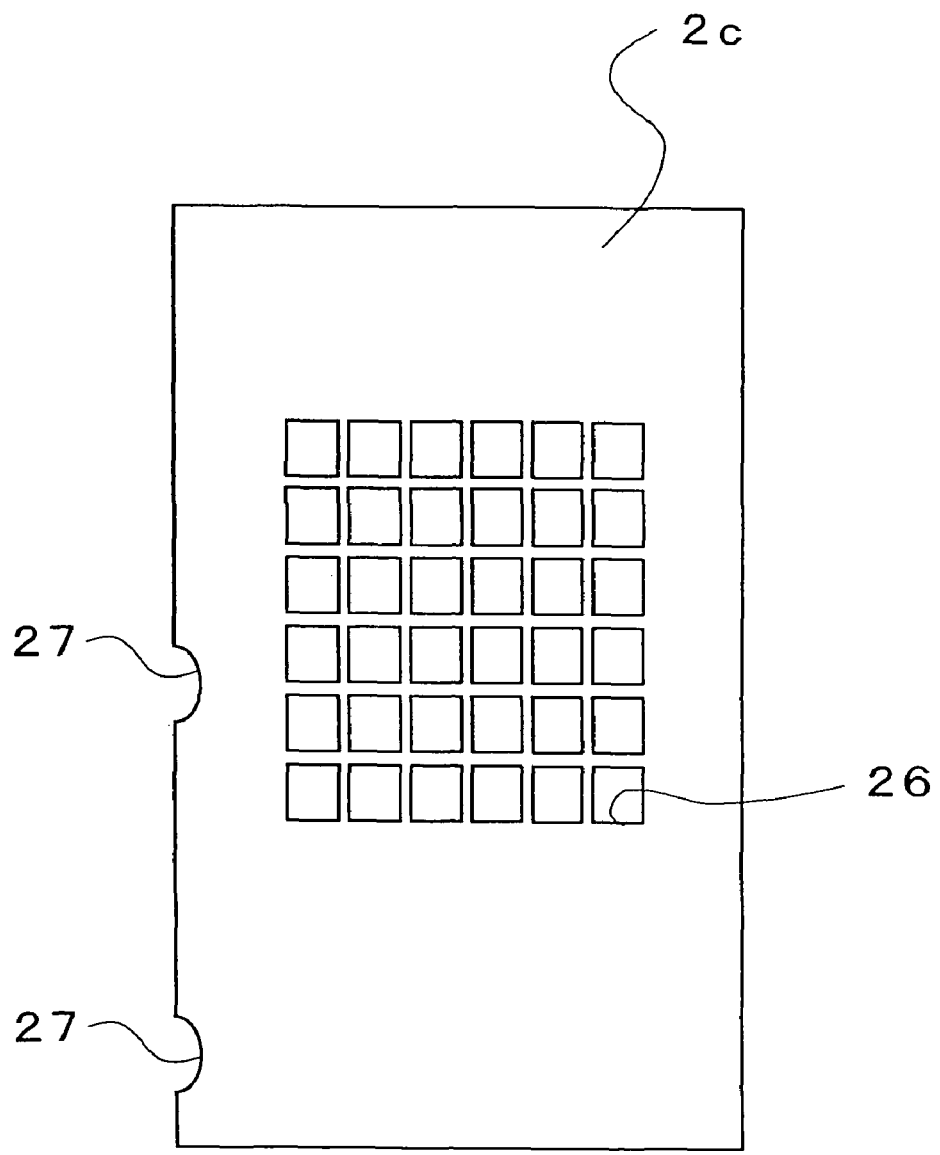
FIG. 6 A plan view of the lid member covering part of the rear housing member, as seen from the back side thereof.

FIG. 6 is a plan view of the lid member 2c, as seen from the back side thereof. The lid member 2c is removably fitted to the rear housing member 2b, and serves as a cover that covers part of the rear face of the rear housing member 2b. This lid member 2c has an inlet 26 and cable clearances 27. The inlet 26 consists of a plurality of holes (for example, rectangular holes) through which air outside the main unit 2 is sucked in as the blowing means 9 is driven. The inlet 26 is formed in a position corresponding to the air introduction port 22 of the rear housing member 2b.

The cable clearances 27 are for permitting the wiring (the connection cable 92) for connecting between the cigarette lighter power outlet 91 provided inside the vehicle and the plug receptacle 25 to be laid therethrough. In this embodiment, a plurality of cable clearances 27 are provided at different levels in the height direction of the main unit. The height (depth) of the beverage container holder 90 provided inside the vehicle as measured when it is pulled out varies with the type and manufacturer of the vehicle and with the type of the beverage container holder itself. Accordingly, if only one cable clearance 27 is provided, depending on the beverage container holder 90, it may happen that the wiring from the vehicle-mounted air purifier 1 held therein cannot be laid adequately. By contrast, if more than one cable clearances 27 are provided at different levels in the height direction of the main unit 2, the wiring can be laid adequately to fit the type (depth) of the beverage container holder 90. This makes it possible to apply the vehicle-mounted air purifier 1 of this embodiment to any type of beverage container holder 90.

To the inner surface of the lid member 2c (the rear housing member 2b side surface thereof), a filter (not illustrated) is fitted so as to cover the inlet 26 from inside. When air is sucked in, this filter removes dust from the air.

(1-3. Light Guide Member)

Figure 7:
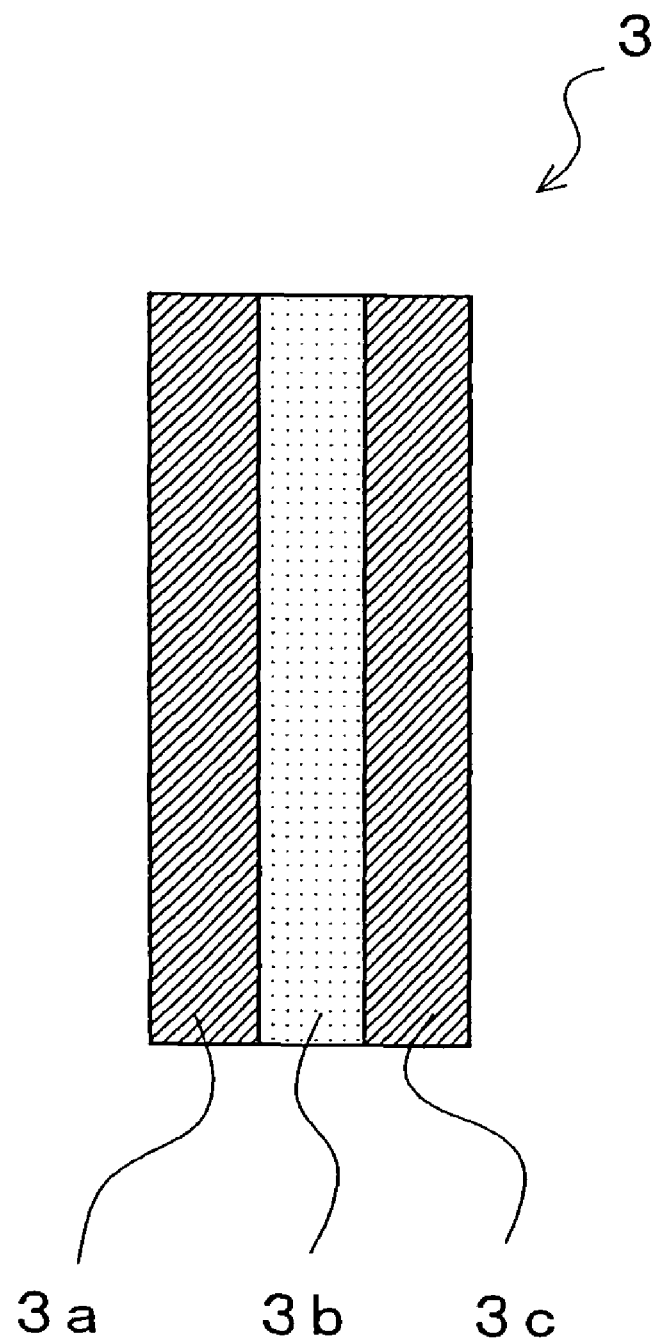
FIG. 7 A sectional view of the light guide member shown in FIG. 2, taken along line A-A'.

Next, the light guide member 3 will be described. The light guide member 3 shown in FIG. 2 is for propagating the light emitted form LEDs 52 and 53 (see FIG. 10) provided on the display circuit board 5, which will be described later. FIG. 7 is a sectional view of the light guide member 3 shown in FIG. 2, taken along line A-A'. As shown in this figure, the light guide member 3 has a three-layer structure in which a light guide plate 3a, a diffusive sheet 3b, and a light guide plate 3c are laid on one another in this order.

As will be described later, the LEDs 52 and 53 are lit according to the operation mode of the ion generator 4. Thus, the light guide member 3 forms a display section that gives indications of the different operation modes described earlier. The provision of this light guide member 3 serving as a display section permits the user to recognize the current operation mode of the ion generator 4 easily and correctly simply by viewing the light guide member 3.

In this embodiment, the light guide member 3 is formed along the face at which the front and rear housing members 2a and 2b are bonded together. This permits the light guide member 3 to be fitted to the main unit 2 easily. Specifically, the light guide member 3 can be fitted to the main unit 2 simply by sandwiching the light guide member 3 between the front and rear housing members 2a and 2b.

Moreover, the light guide member 3 is formed substantially in a U-like shape so as to lie along the face at which the front and rear housing members 2a and 2b are bonded together. This permits the light guide member 3, when sandwiched between the front and rear housing members 2a and 2b, to extend over the top and side (circumferential) faces of the main unit 2.

Forming the light guide member 3 substantially in a U-like shape so that it extends over a plurality of faces that form the main unit 2 in this way permits the user to view the light guide member 3 from a fairly wide range of angles. That is, the user can view the light guide member 3, for example, from obliquely above and also from the side. Thus, irrespective of where the main unit 2 (the vehicle-mounted air purifier 1) is placed inside the vehicle, the user can recognize the current operation state with ease and without fail. Moreover, in a case where a plurality of people are present inside the vehicle, thanks to the light guide member 3 being formed so as to lie over a plurality of faces of the main unit 2, everyone can view the light guide member 3 even though viewing it from a different direction.

(1-4. Ion Generator)

Next, the ion generator 4 will be described. The ion generator 4 generates positive ions, negative ions, or both positive and negative ions through electric discharge. A more detailed description will be given below.

Figure 8:
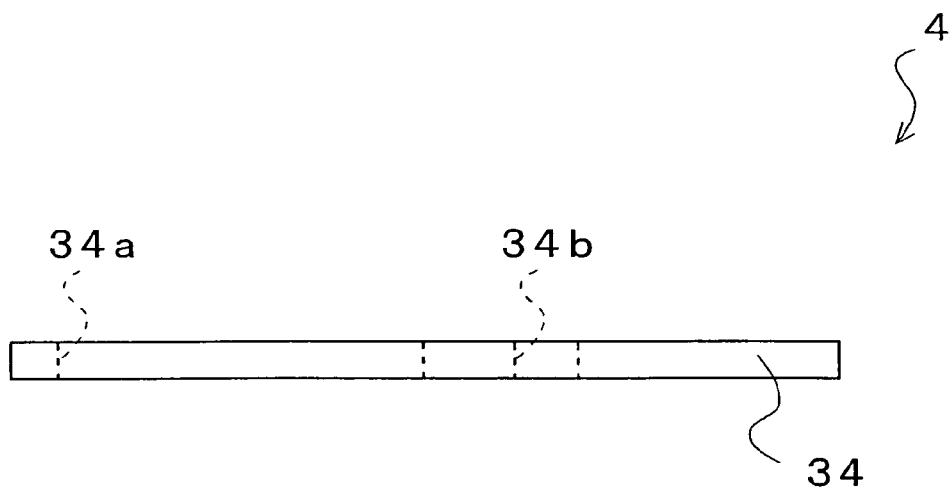
FIG. 8 A side view showing, in an exploded state, an outline of the construction of the ion generator incorporated in the main unit.
Figure 8:
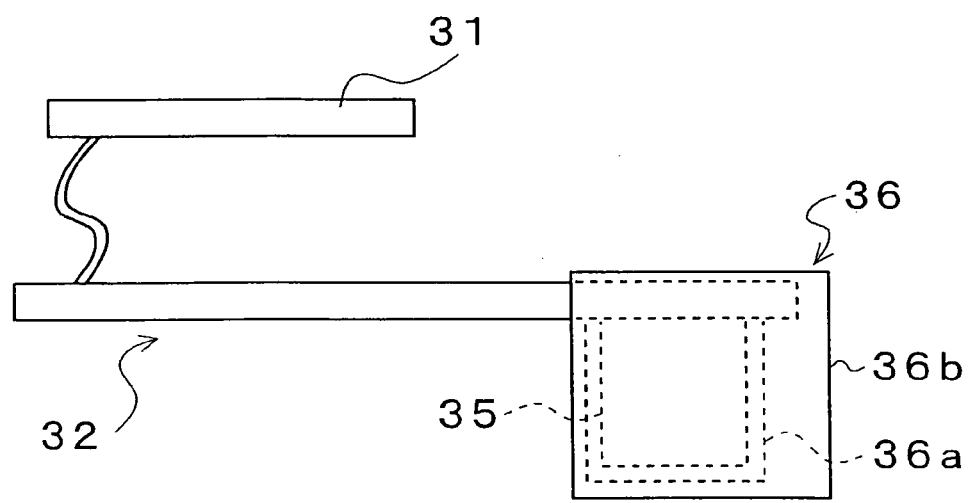
Figure 8:
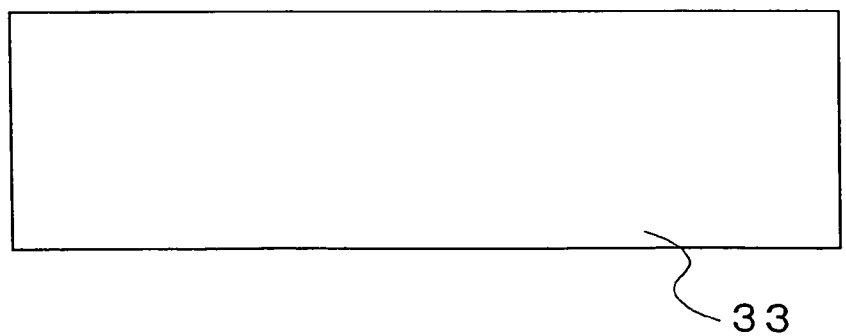

FIG. 8 is a side view showing an outline of the construction of the ion generator 4, in an exploded state. The ion generator 4 has an ion generating element 31 and a circuit board 32, which serves as a drive circuit for driving it, housed inside a casing 33 that is covered with a lid 34. In the lid 34, there are formed an opening 34a into which the ion generating element 31 is fitted, and an opening 34b through which resin is injected to seal the inside.

Figure 9:
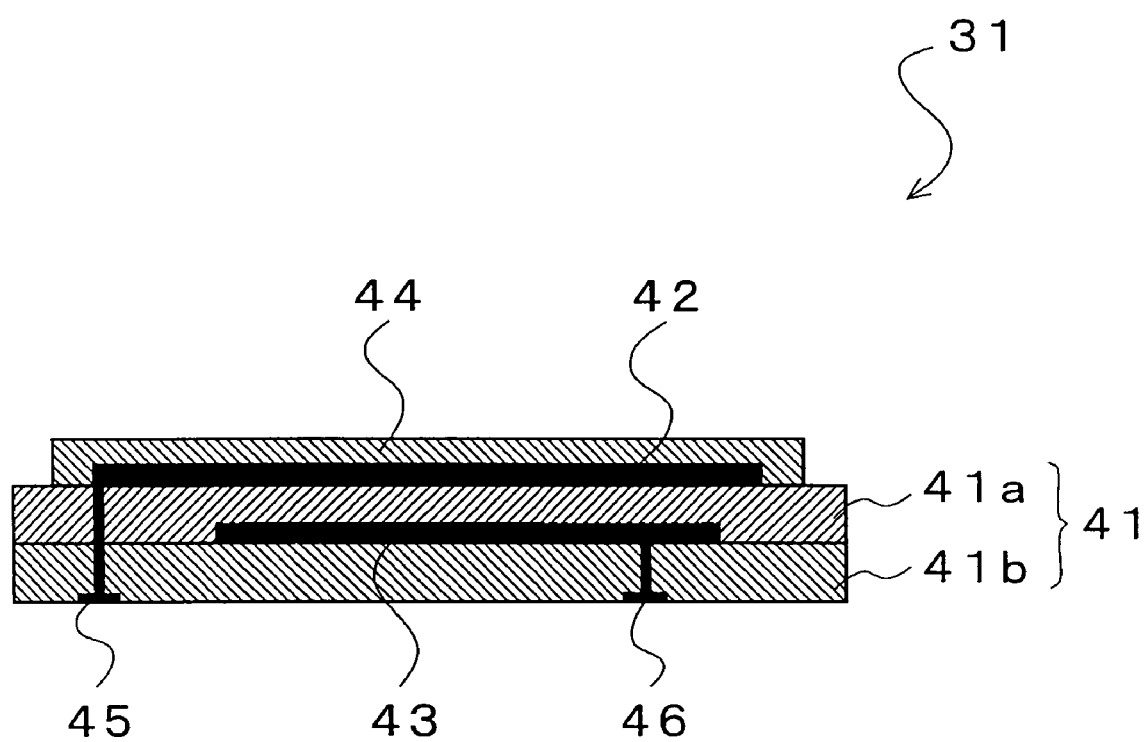
FIG. 9 A sectional view showing an outline of the construction of the ion generating element provided in the ion generator.

As shown in FIG. 9, the ion generating element 31 has a dielectric member 41 composed of an upper dielectric member 41a and a lower dielectric member 41b bonded together. On the surface of the upper dielectric member 41a opposite to the lower dielectric member 41b, a discharge electrode 42 is formed. This discharge electrode 42, as seen in a plan view, is shaped like a lattice and, in each mesh of the lattice, has needle-like electrodes formed so as to protrude along the surface.

On the surface of the lower dielectric member 41b facing the upper dielectric member 41a, an induction electrode 43 is formed. The induction electrode 43 is bent as seen in a plan view (so as to have, for example, a U-like shape). The induction electrode 43 is so formed as to overlap the needle-shaped tips of the discharge electrode 42. On the surface of the upper dielectric member 41a, a surface protection layer 44 is formed so as to cover the discharge electrode 42.

On the surface of the lower dielectric member 41b opposite to the upper dielectric member 41a, there are formed a discharge electrode contact 45 via which electric power is fed to the discharge electrode 42 and an induction electrode contact 46 via which electric power is fed to the induction electrode 43.

In the construction described above, when the circuit board 32 applies a high alternating-current voltage between the discharge electrode 42 and the induction electrode 43 via the discharge electrode contact 45 and the induction electrode contact 46, corona discharge occurs near the discharge electrode 42. This ionizes the air around the discharge electrode 42, generating, for example, $H^+(H_2O)_m$ (where m is a natural number) as positive ions and $O_2^-(H_2O)_n$ (where n is a natural number) as negative ions.

Here, if the alternating-current voltage applied between the discharge electrode 42 and the induction electrode 43 is such that a positive and a negative voltage are applied for equal periods of time, equal numbers of positive and negative ions are generated. This is the "clean mode" operation. On the other hand, if the applied voltage is such that a positive voltage is applied for a longer period of time than a negative voltage, negative ions are generated in a higher proportion than positive ions. This is the "ion control mode" operation.

In the ion generating element 31, ions are generated through corona discharge that takes place near the discharge electrode 42. Thus, in the ion generating element 31, the surface on which the discharge electrode 42 is formed is the discharge surface. In this embodiment, the ion generator 4 has this discharge surface arranged vertically (in the height direction of the main unit 2) inside the main unit 2 so as to face the rear housing member 2b (see FIG. 2).

The circuit board 32 shown in FIG. 8 includes the drive circuit for driving the ion generator 4. This drive circuit includes a step-up coil 35 as well as circuit components such as capacitors and semiconductor devices. The step-up coil 35 steps up the voltage fed from the power source (for example, the cigarette lighter power outlet 91) to drive the ion generator 4.

When the ion generator 4 is driven, the step-up coil 35 produces radiating noise. Such radiating noise may cause malfunctioning of vehicle-mounted instruments (such as various meters and safety devices). Considering that more and more emphasis is placed on the safety of vehicles nowadays, it is undesirable to leave radiating noise uncontrolled.

Accordingly, in this embodiment, the step-up coil 35 provided on the circuit board 32 is covered with a shielding member 36. This shielding member 36 is composed of two shielding members 36a and 36b that are formed as, for example, metal covers. The shielding members 36a and 36b are each shaped like a rectangular or circular cup, and are each formed airtight except at an opening formed therein. The shielding member 36b is formed larger in volume than the shielding member 36a.

The shielding member 36a is so provided on the circuit board 32 as to cover the step-up coil 35 provided on the circuit board 32 from the side (the casing 33 side) of the step-up coil 35 at which it is provided on the circuit board 32. On the other hand, the shielding member 36 is inserted from a direction along the surface of the circuit board 32 so as to cover, along with the circuit board 32, the shielding member 36a covering the step-up coil 35.

The provision of this shielding member 36 helps reduce the leakage of the radiating noise, if any, generated by the step-up coil 35, and thus helps almost eliminate malfunctioning of vehicle-mounted instruments. In particular, by building the shielding member 36 with two shielding members 36a and 36b and arranging them so that they cover the step-up coil 35 from both sides of the circuit board 32 on which the step-up coil 35 is provided, it is possible to surely reduce the leakage of radiation noise not only on the step-up coil 35 side of the circuit board 32 but also on the opposite side thereof. This helps surely eliminate malfunctioning of instruments.

(1-5. Display Circuit Board)

Figure 10:
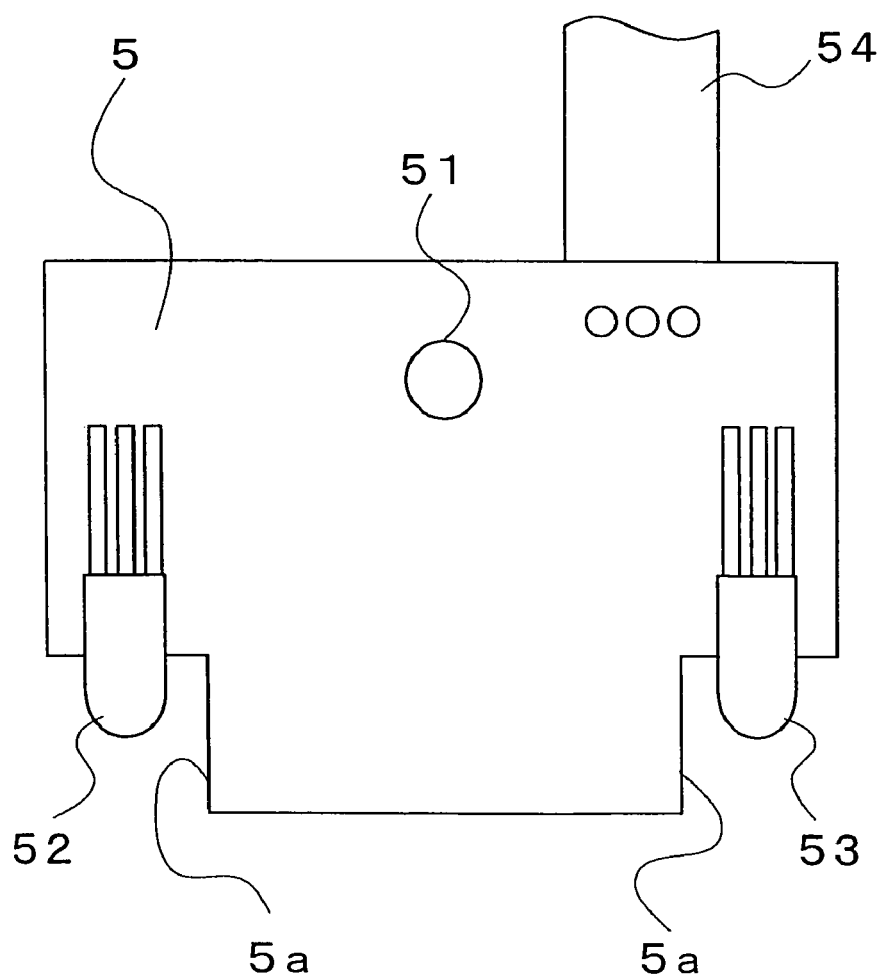
FIG. 10 A plan view showing an outline of the construction of the display circuit board provided in the main unit.

Next, the display circuit board 5 will be described. FIG. 10 is a plan view showing an outline of the construction of the display circuit board 5. The display circuit board 5 is for displaying indications corresponding to the operation mode of the vehicle-mounted air purifier 1. This display circuit board 5 is provided with an operation switch 51, LEDs 52 and 53, and, though unillustrated, a plurality of connection terminals.

The operation switch 51 is for turning the operation of the vehicle-mounted air purifier 1 on and off, and is operated as the operation button 11 provided on the main unit 2 is pressed. The operation switch 51 generates a switching signal, which is fed by way of a cable 54 to the control circuit board 7.

The LEDs 52 and 53 are light-emitting elements that emit light of colors corresponding to the operation mode of the vehicle-mounted air purifier 1, and are supported on the display circuit board 5. In this embodiment, the LEDs 52 and 53 are each a dual-color light-emitting element that emits either blue or green light. For example, the LEDs 52 and 53 emit blue light in "clean mode" operation, green light in "ion control mode" operation, and blue and green light alternately at predetermined time intervals (for example, at five-minute intervals) in "automatic mode" operation.

The LEDs 52 and 53 have their tips (light-emitting portions) bent to lie along the surface of the display circuit board 5. Correspondingly, the parts of the display circuit board 5 which correspond to the tips of the LEDs 52 and 53, i.e., two corner parts of the display circuit board 5, are cut out to form cut portions 5a. This permits the light emitted from the LEDs 52 and 53 to shine not only the surface of the display circuit board 5 on which the LEDs 52 and 53 are provided but also, through the cut portions 5a, the opposite surface thereof. Thus, in a case where the display circuit board 5 is arranged parallel to the top and bottom faces of the display circuit board 5 so that the LEDs 52 and 53 point toward the rear housing member 2b, the light therefrom reaches not only the upper part of the main unit 2 but also the light guide member 3 located below. In this way, the light emitted from the LEDs 52 and 53 can be effectively used to enhance the visibility of the light guide member 3 as a whole.

Thus, the vehicle-mounted air purifier 1 of the invention can be said to be constructed as follows. There is provided a light-emitting element (the LEDs 52 and 53) that emits light of a color to be displayed in a display section (the light guide member 3) and that feeds the light to the display section. There is also provided a display circuit board 5 that supports the light-emitting element. The display circuit board 5 has a corner thereof cut out to form a cut portion 5a, and supports the light-emitting element in such a way that the light emitted therefrom travels through the cut portion 5a to the rear and side faces of the circuit board.

(1-6. Power Supply Circuit Board)

The power supply circuit board 6 is for feeding the electric power fed from the power source (the cigarette lighter power outlet 91 or a battery) to the relevant parts inside the main unit 2. On this power supply circuit board 6, there are formed power source connection terminals, connection cable connection terminals, etc. The power source connection terminals are electrically connected to the plug receptacle 25 provided in the rear housing member 2b of the main unit 2. The connection cable connection terminals are for electrically connecting the power supply circuit board 6 to the control circuit board 7 by way of a connection cable (leads).

(1-7. Control Circuit Board)

The control circuit board 7 is for controlling the operation of the various parts inside the main unit 2. On this control circuit board 7, there are formed an IC chip, connection cable connection terminals, etc. The connection cable connection terminals are for electrically connecting the control circuit board 7 to the display circuit board 5 and the power supply circuit board 6 by way of a connection cable (leads). The control circuit board 7 controls the driving of the ion generator 4 and the blowing means 9 according to the operation mode selected as the operation button 11 is pressed.

(1-8. Support Plate)

Figure 11:
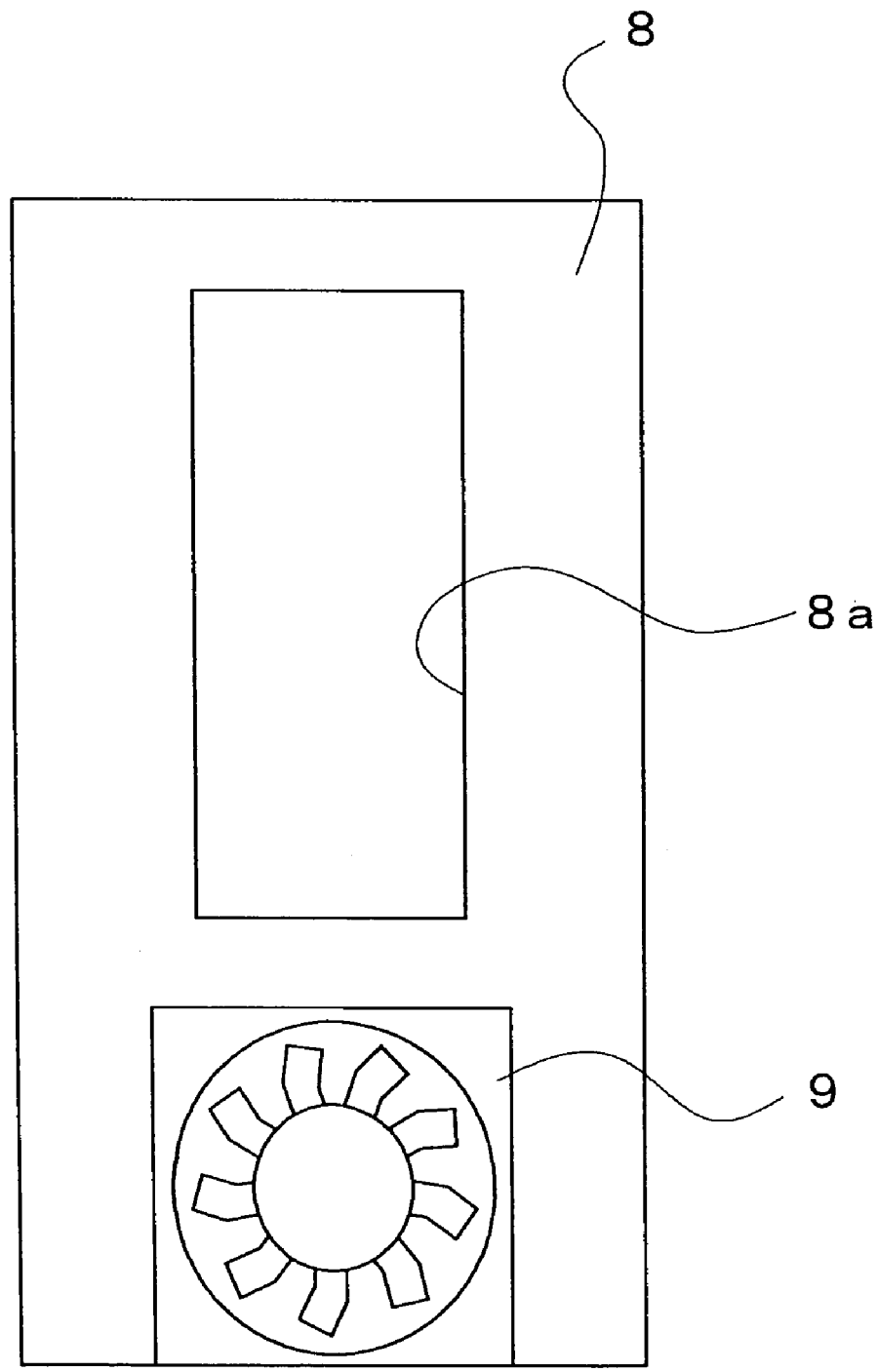
FIG. 11 A plan view of the support plate provided in the main unit, in a state supporting the blowing means.
Figure 12:
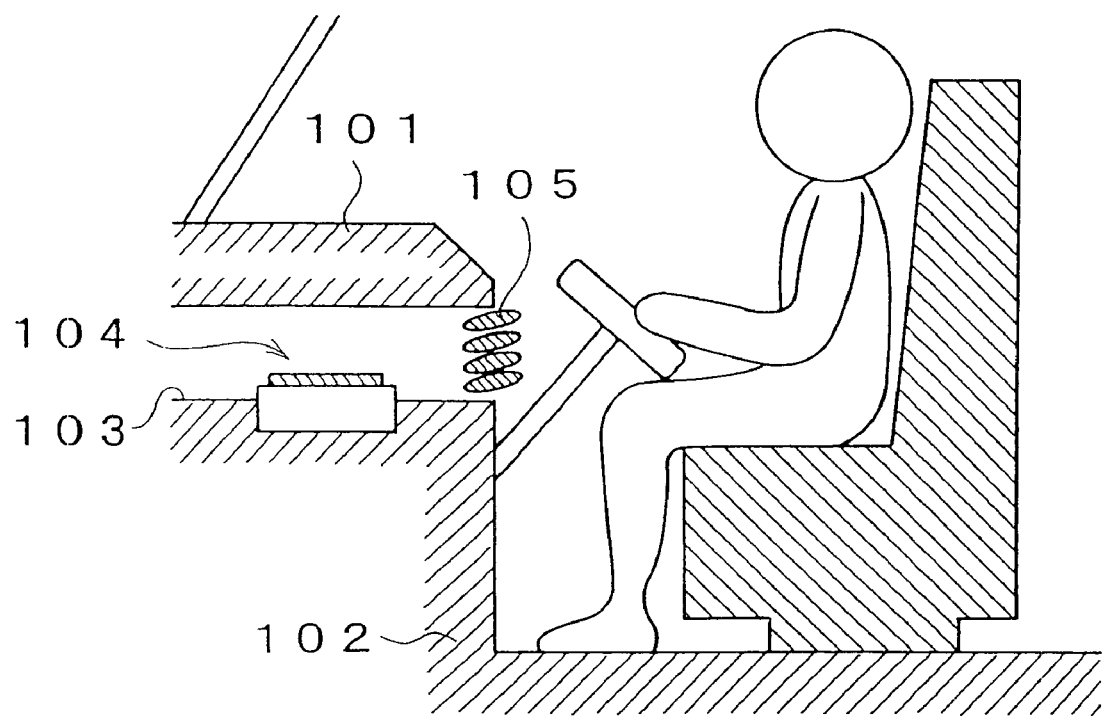
FIG. 12 A diagram schematically illustrating a conventional construction in which an ion generator is arranged in an air passage inside a vehicle.

FIG. 11 is a plan view of the support plate 8, as seen from the rear housing member 2b side. The support plate 8 is for supporting the blowing means 9 inside the main unit 2, and is arranged inside the main unit 2 in such a way that the surface of the support plate 8 is perpendicular to the top and bottom faces of the main unit 2. The support plate 8 has a rectangular opening 8a formed therein that permits the discharge surface of the ion generator 4 (see FIG. 2) to be exposed toward the blowing means 9. Thus, while the support plate 8 supports the blowing means 9, air is fed from the blowing means 9 through the opening 8a to the discharge surface of the ion generator 4, and the ions generated by the ion generator 4 are fed through the opening 8a toward the blowing means 9. In this way, the air containing ions can be discharged out of the ion generator 4.

(1-9. Blowing Means)

The blowing means or blower 9 is for sucking in air from outside the main unit 2 to feed it to the ion generator 4. The blowing means or blower 9 is composed of a drive motor and a fan, and is supported by the support plate 8 inside the main unit 2. The blowing means 9 may be, for example, a compact type designed for use in a personal computer. The provision of this blowing means 9 inside the main unit 2 permits the ion generator 4 to generate both positive and negative ions by causing electric discharge in the air fed from the blowing means 9. Moreover, it is also possible to discharge the ions generated by the ion generator 4 out of the main unit 2 by carrying them on the flow of air fed from the blowing means 9.

(2. Assembly and Fitting)

Next, how the vehicle-mounted air purifier 1 constructed as described above is assembled and fitted inside a vehicle will be described with reference to FIGS. 1 to 3.

First, the light guide member 3 is placed on the face of the front housing member 2a at which it is bonded to the rear housing member 2b. Then, the ion generator 4 is connected to the control circuit board 7, and is then fitted in the ion generator support portion 12. Then, the control circuit board 7 is connected to the display circuit board 5 and the power supply circuit board 6 respectively with connection cables, and then the display circuit board 5, power supply circuit board 6, and control circuit board 7 are fitted into the display circuit board support portion 13, power supply circuit board support portion 14, and control circuit board support portion 15, respectively.

Next, the support plate 8 having the blowing means 9 fitted thereon is fitted on the front housing member 2a in such a way that the discharge surface of the ion generator 4 is exposed through the opening 8a. Then, the rear housing member 2b is bonded to the front housing member 2a. Subsequently, the operation button 11 is inserted into a predetermined hole formed in the front housing member 2a of the main unit 2, and a display sheet is bonded to the top face of the front housing member 2a. Lastly, one end of the connection cable 92 is plugged into the plug receptacle 25 of the rear housing member 2b, and then the lid member 2c is fitted to the rear housing member 2b. At this time, whichever of the cable clearances 27 suits the holding depth of the beverage container holder 90 in which the vehicle-mounted air purifier 1 is going to be held is selected, and then, with the connection cable 92 taken out through that cable clearance, the lid member 2c is fitted to the rear housing member 2b.

The vehicle-mounted air purifier 1 is held in the beverage container holder 90 provided inside the vehicle, and then the other end of the connection cable 92 is plugged into the cigarette lighter power outlet 91 provided inside the vehicle. Now, the fitting of the vehicle-mounted air purifier 1 inside the vehicle is complete.

(3. Operation)

The vehicle-mounted air purifier 1 operates as follows.

With the vehicle-mounted air purifier 1 held in the beverage container holder 90 as described above, the operation button 11 is pressed to select the desired operation mode. Now, electric power is fed via the power supply circuit board 6 to the ion generator 4 and to the blowing means 9, and thus these start operating.

As the blowing means 9 is driven, air outside the main unit 2 is taken into the main unit 2 through the inlet 26, filter, and air introduction port 22 of the main unit 2, and is fed to the discharge surface of the ion generator 4. At this time, the air sent from the blowing means 9 collides with the guide plate 23, and strikes the discharge surface of the ion generator 4 at an acute angle.

On the other hand, the ion generator 4 operates according to the selected operation mode to generate positive and negative ions, for example, in equal proportions or in proportions rich in negative ions. At this time, the LEDs 52 and 53 emit light of the color corresponding to the selected operation mode.

The ions generated by the ion generator 4 are mixed with the rest of the air fed from the blowing means 9. Here, since the air fed from the blowing means 9 enters the ion generator 4 from obliquely below relative to the discharge surface. Thus, the air mixed with the ions flows upward along the discharge surface, is then compressed by the compressing member 24 (so that the flow rate is narrowed), and is then, with increased flow speed, discharged through the outlet 21 out of the main unit 2. The air containing ions thus released through the outlet 21 is, so long as the vehicle-mounted air conditioner is being driven, spread around the inside of the vehicle by being carried by the air for air-conditioning that is blown out through the outlet 93 provided inside the vehicle.

For example, when positive and negative ions are released into the air inside a vehicle and attach to the surface of airborne bacteria floating in the air, the chemical reactions expressed by formulae (1) to (3) below take place. As a result, positive and negative ions generate hydrogen peroxide ($H_2O_2$) or hydroxyl radical (.OH), which are both radicals. In formulae (1) to (3) below, m, m', n, and n' each represent a natural number.

$$H^+(H_2O)_m + O_2^-(H_2O)_n \rightarrow .OH + 1/2\, O_2 + (m+n)H_2O \quad (1)$$

$$H^+(H_2O)_m + H^+(H_2O)_{m'} + O_2^-(H_2O)_n + O_2^-(H_2O)_{n'} \rightarrow 2.OH + O_2 + (m+m'+n+n')H_2O \quad (2)$$

$$H^+(H_2O)_m + H^+(H_2O)_{m'} + O_2^-(H_2O)_n + O_2^-(H_2O)_{n'} \rightarrow H_2O_2 + O_2 + (m+m'+n+n')H_2O \quad (3)$$

The above-mentioned radical $H_2O_2$ or .OH is extremely active, exerting a decomposing effect on airborne bacteria, which are thereby destroyed. In this way, the air inside the vehicle is purified, that is, airborne bacteria present in the air inside the vehicle are deactivated and removed. Here, "deactivate" denotes killing, removing, and reducing airborne bacteria and decomposing and removing viruses.

On the other hand, when the vehicle-mounted air purifier 1 is driven in ion control mode, it generates ions in proportions rich in negative ions. In this case, negative ions exert a relaxing effect on humans.

(4. Advantages)

As described above, the vehicle-mounted air purifier 1 of this embodiment is a vehicle-mounted air purifier that is mounted on a vehicle and that includes a main unit 2 incorporating an ion generator 4 that generates positive ions, negative ions, or both positive and negative ions, and, here, the main unit is removably arranged within the passenger space inside the vehicle (for example, a beverage container holder 90). Thus, the ions generated by the ion generator 4, after being discharged out of the main unit 2, are released directly into the passenger space inside the vehicle. This greatly reduces the number of times that the ions collide with exterior components as compared with, for example, when the ion generator is arranged in a passage inside an outlet of air-conditioned air, in which case the ions collide with the passage and the outlet. Thus, assuming that the ion generating performance of the ion generator 4 (the number of ions it generates per unit time) is constant, it is possible to feed ions into the passenger space with higher efficiency than can conventionally be achieved.

Moreover, the main unit 2 is arranged within the passenger space so that it is removable as an independent unit. Thus, even when the ion generator 4 breaks down or otherwise its replacement becomes necessary, the arranged ion generator 4 can be removed readily and replaced easily. Moreover, a vehicle that is originally not equipped with an ion generator can later be fitted with one. This helps enhance usability.

(5. Other Features)

The above description deals with a construction in which a desired operation mode is selected as the operation button 11 is operated by being pressed. It is to be understood, however, that the present invention can be implemented in any other manner.

For example, when a driver is driving a vehicle at high speed (for example, 80 km/h or more), or is driving a vehicle at low speed (for example, 10 km/h or less) for a long time, the driver feels much stress or frustration. By contrast, when a driver is driving a vehicle at moderate speed (for example, 30 km/h to 40 km/h), the stress on the driver is comparatively mild. On the other hand, the vibration of a vehicle monotonically increases as the speed at which it is driven increases. Thus, if the vibration of a vehicle can be monitored using a vibration sensor, the speed at which the vehicle is traveling can be roughly grasped.

Accordingly, a vibration sensor (monitoring means) for monitoring the vibration of a vehicle, which is supposed to be commensurate with the speed at which it is traveling, may be provided so that, according to the vibration monitored by the vibration sensor, the control circuit board 7 (a controller) automatically switches the operation modes. For example, the control circuit board 7 may be so configured as to perform control such that, when the vibration sensor detects vibration that indicates that the vehicle is traveling at high or low speed, "ion control mode" is selected to produce a highly relaxing effect by the action of negative ions and, when the vibration sensor detects vibration that indicates that the vehicle is traveling at medium speed, "clean mode" is selected. This helps eliminate the trouble required for the driver to switch operation modes by pressing the operation button 11 while driving, and makes it possible to automatically condition the air inside the vehicle to suit the driver's mental condition.

In particular, in a case where time counting means (a timer) for counting the time for which the vehicle is traveling at low speed is provided in the main unit 2, the control circuit board 7 may be so configured that, when the vibration sensor mentioned above detects the vehicle traveling at low speed and in addition the time counting means detects it traveling at low speed for a predetermined length of time or more, the operation mode is automatically switched to "ion control mode". In this case, the vehicle is recognized to be traveling in congested traffic, and accordingly, by releasing a comparatively large number of negative ions into the space inside the vehicle in "ion control mode", it is possible to alleviate the driver's frustration to encourage safe driving.

The vehicle-mounted air purifier 1 of the invention may be modified in any of the following manners.

In the vehicle-mounted air purifier 1 of the invention configured as described above, advisably, air is sucked in through one face of the main unit 2 by the blowing means 9, and both the positive and negative ions generated by the ion generator 4 are released into the air through the outlet 21 in the top face of the main unit 2 so that airborne bacteria floating in the air are removed.

In the vehicle-mounted air purifier 1, advisably, the air sucked in by the blowing means 9 is made to strike the discharge surface of the ion generator 4 from an oblique direction so as to be released through the outlet 21 so that airborne bacteria floating in the air are removed.

In the outlet 21 of the vehicle-mounted air purifier 1, advisably, discharge regulating means for regulating the flow of air there is provided so that air containing the ions generated by the ion generator 4 is blown out frontward relative to the main unit 2.

In the vehicle-mounted air purifier 1, advisably, the ion generator 4 is so arranged that the discharge surface thereof is located near the air outlet of the blowing means 9.

In the vehicle-mounted air purifier 1, advisably, flow rate regulating means (the compressing member 24) is provided for regulating the flow rate of the air flowing from the ion generator 4 to the outlet 21 so that the area through which the air flowing from the ion generator 4 to the outlet 21 is smaller than the area through which the air fed from the blowing means 9 to the ion generator 4 passes.

In the vehicle-mounted air purifier 1, advisably, the main unit 2 is divided into a front and a rear part, and a display section (the light guide member 3) for displaying indications corresponding to different operation modes is formed at the face at which the main unit 2 is divided.

Advisably, the display section is so formed as to extend over the top and circumferential faces of the main unit 2.

Advisably, the power source (the power supply circuit board 6 and the plug receptacle 25) from which the vehicle-mounted air purifier 1 is operated can be connected to a cigarette lighter power outlet 91 provided inside the vehicle.

Advisably, there are formed, at different levels in the height direction of the main unit 2, a plurality of cable clearances 27 through one of which to take out of the main unit 2 the connection cable for connecting the power source from which the vehicle-mounted air purifier 1 is operated to the cigarette lighter power outlet 91 provided inside the vehicle.

Advisably, noise reducing means (the shielding member 36) is provided for reducing the radiating noise radiated from the step-up coil 35 provided on the circuit board 32 in the ion generator 4.

INDUSTRIAL APPLICABILITY

The vehicle-mounted air purifier 1 of the invention finds application as an air purifier for purifying the air inside a vehicle such as a passenger car, bus, taxi, or truck.

The invention claimed is:

1. An air purifier for mounting on a vehicle, comprising
a main unit incorporating an ion generator that generates positive ions, negative ions, or both positive and negative ions,
wherein the main unit is removably arranged within a passenger space inside the vehicle,
wherein the main unit further includes a blower for sucking in air outside the main unit to feed the air to the ion generator,
wherein, in the ion generator, a discharge surface on which ions are generated by electric discharge is arranged along a direction in which air is blown out by the blower,
wherein the main unit further includes a guide plate for guiding the air blown out from the blower so that the air strikes the discharge surface at an acute angle, and
wherein the main unit further includes a display section on which an indication corresponding to an operation mode of the ion generator is displayed.

2. The air purifier of claim 1,
wherein the main unit is so shaped as to fit in a beverage container holder provided inside the vehicle.

3. The air purifier of claim 1,
wherein the main unit is formed in a shape that fits in a beverage container holder provided inside the vehicle.

4. The air purifier of claim 3,
wherein the main unit is cylindrical.

5. The air purifier of claim 2,
wherein the beverage container holder is located below a first outlet through which air for air-conditioning of an inside of the vehicle is blown out,
wherein the main unit includes a second outlet through which air containing ions generated by the ion generator is blown out, and
wherein the second outlet is so located that, when the main unit is held in the beverage container holder, the air containing the ions is mixed with the air for air-conditioning that is blown out through the first outlet.

6. The air purifier of claim 1,
wherein the main unit further includes a compressing member for compressing air that is discharged out of the main unit through the ion generator.

7. The air purifier of claim 1,
wherein the main unit is composed of a plurality of separate housing members bonded together, and
wherein the display section is formed along a face at which the separate housing members are bonded together.

8. The air purifier of claim 7,
wherein the display section is so formed as to extend over a plurality of faces forming the main unit.

9. The air purifier of claim 1, further comprising:
a light-emitting device that emits light of a color displayed on the display and that feeds the light to the display section; and
a display circuit board that supports the light-emitting device,
wherein the display circuit board has a corner thereof cut out to form a cut portion, and
wherein the display circuit board supports the light-emitting device so that the light emitted from the light-emitting device travels through the cut portion to behind the display circuit board.

10. The air purifier of claim 1,
wherein the main unit further includes a connection portion that is connected to a cigarette lighter power outlet provided inside the vehicle.

11. The vehicle mounted air purifier of claim 10,
wherein the main unit includes a plurality of ports through which to run a cable for connecting between the cigarette lighter power outlet and the connection portion, the ports being located at different levels in a height direction of the main unit.

12. The air purifier of claim 1,
wherein the main unit further includes
a voltage step-up coil for stepping up a voltage fed from a power source to drive the ion generator and
a shielding member that covers the voltage step-up coil.

13. The air purifier of claim 12,
wherein the shielding member covers the voltage step-up coil from both sides of a circuit board on which the voltage step-up coil is arranged.

14. The air purifier of claim 1,
wherein an operation mode of the ion generator is changed according to a traveling speed of the vehicle in which the main unit is mounted.

15. The air purifier of claim 1, further comprising:
monitoring means for monitoring vibration commensurate with a traveling speed of the vehicle in which the main unit is mounted, and
a controller that changes the operation mode of the ion generator according to a degree of the vibration monitored by the monitoring means.

16. The air purifier of claim 1, further comprising:
a light-emitting device that is lit according to an operation mode of the ion generator;
a light guide member that propagates light emitted from the light-emitting device; and
a circuit board that supports the light-emitting device,
wherein the light guide member is formed substantially in a U-like shape so as to extend along a top and circumferential faces of the main unit,
wherein the circuit board is arranged parallel to the top face of the main unit, and supports the light-emitting device such that the light emitted from the light-emitting device reaches not only a surface of the circuit board facing the light-emitting device but also, through a cut portion formed by cutting off a corner part of the circuit board, an opposite face thereof.

17. The air purifier of claim 1, further comprising
a circuit selectable to select a selected operation mode of the ion generator that generates one of positive ions, negative ions, or both positive and negative ions.

* * * * *